United States Patent [19]

Murayama et al.

[11] 4,086,208
[45] Apr. 25, 1978

[54] FLAME RESISTANT POLYESTERS

[75] Inventors: Ken Murayama; Takao Kashihara, both of Otsu, Japan

[73] Assignee: Toyo Boseki Kabushiki Kaisha, Japan

[21] Appl. No.: 648,975

[22] Filed: Jan. 14, 1976

[30] Foreign Application Priority Data

Jan. 17, 1975 Japan .................................... 50-7072
May 16, 1975 Japan .................................... 50-59061

[51] Int. Cl.$^2$ ...................... C08G 63/20; C08G 79/04
[52] U.S. Cl. ............................ 260/47 C; 260/45.7 P; 260/47 P; 260/49; 260/75 P
[58] Field of Search ................ 260/75 P, 47 P, 47 C, 260/45.7 P, 49

[56] References Cited

U.S. PATENT DOCUMENTS

| 3,406,153 | 10/1968 | Eaton | 260/75 P |
| 3,412,070 | 11/1968 | Jakob et al. | 260/75 P |
| 3,853,819 | 12/1974 | Herwig et al. | 260/75 P |
| 3,928,283 | 12/1975 | Masai et al. | 260/45.7 P |
| 3,941,752 | 3/1976 | Kleiner et al. | 260/75 P |

Primary Examiner—Lucille M. Phynes
Attorney, Agent, or Firm—Birch, Stewart, Kolasch and Birch

[57] ABSTRACT

Novel flame resistant polyesters provided with improved moldability. The polyester comprising a combination of an aromatic dicarboxylic acid or an ester-forming derivative thereof, a diol or an ester-forming derivative thereof, and a particular phosphorus compound having at least two ester-forming functional groups. The content of phosphorus in the polyester is about 500–50,000 ppm.

9 Claims, No Drawings

FLAME RESISTANT POLYESTERS

BACKGROUND OF INVENTION

This invention relates to an improvement in the flame resistance of polyesters, and more particularly to novel flame resistant polyesters prepared by adding a specific phosphorus compound having at least two ester-forming functional groups during the preparation of aromatic polyesters.

In recent years, from the fireproof viewpoint it is increasingly required to provide various synthetic fibers and plastic products with flame resistance. An aromatic polyester such as polyethyleneterephthalate is one of the polymers which is now largely used as molded articles such as fiber, film, and board. Accordingly it has remained desirable to develop an aromatic polyester having flame resistance.

Conventional methods for providing a molded article consisting of aromatic polyester with the flame resistance are listed below.

(1) applying a flame resistant coating to the surface of the molded article.

(2) compounding and kneading a flame resistant agent during the molding of the article.

(3) mixing a flame resistant agent during the preparation of polyester.

(4) copolymerizing polyester-forming reagents with a flame resistant agent during the preparation of polyester.

Among these methods the last copolymerizing method is most preferred in principle, because a molded article of polyester copolymerized with a flame resistant agent has the following superior characteristics in comparison with those obtained by the other preceding three methods; complicated operations after molding are obviated, the light resistance and the hand are not adversely affected, the flame resistance is maintained substantially uniform for long periods of time, the toxicity in use is negligible, and so on. For such a copolymerization process a number of phosphorus compounds as the flame resistant agent have hitherto been proposed.

These proposed phosphorus compounds, however, have serious disadvantages; the phosphorus compounds are expensive and thus inconvenient in practice since it is difficult to synthesize them because of their complicated chemical structures, they deactivate catalysts for polymerization to lower the rate of polymerization when added in polymerization systems for polyester, they give rise to side reactions such as formation of ether bonds and gelation, resulting in undesirable polymers having unsatisfactorily low physical properties, and they tend to dissipate from the polymerization systems in the normal polymerization conditions. As the result of this, on the one hand, they are required in greater amounts in order to obtain desirable polymers having the satisfactory flame resistance and, on the other hand, there occurs a pollution problem caused by their dissipation. Though it is intensely desired to manufacture flame resistant polyesters through the copolymerization with phosphorus compounds, a number of problems as described above have prevented the achievement of such a process.

SUMMARY OF INVENTION

Therefore, it is an object of this invention to provide a novel flame resistant polyester by adding a phosphorus compound having a particularly defined structure during the preparation of polyester.

Another object of this invention is to provide a flame resistant polyester having improved properties which can be manufactured under reasonable operating conditions.

A further object of this invention is to provide a polyester suitable for manufacturing the flame resistant fiber. Other objects of this invention will appear hereinafter.

According to a feature of this invention, there is provided a flame resistant polyester comprising a combination of an aromatic dicarboxylic acid or an ester-forming derivative thereof, a diol or an ester-forming derivative thereof, and a phosphorus compound, characterized in that during the preparation of said polyester at least one phosphorus compound having at least two, preferably at least three ester-forming functional groups is added so as to give a content of phosphorus in the range of about 500 to about 50,000 ppm in the resultant polyester. A particularly suitable phosphorus compound in accordance with the first aspect of this invention has the formula:

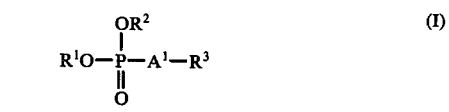

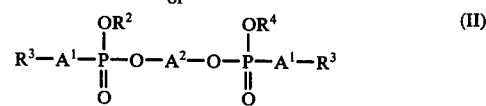

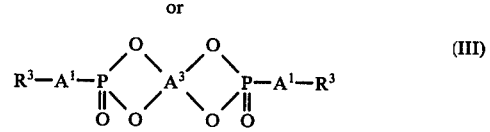

wherein $R^1$, $R^2$, and $R^4$ may be the same or different and represent hydrogen atoms or hydrocarbon groups having 1 to 18 carbon atoms which may contain at least one halogen atom, $R^1$ and $R^2$ being capable of forming a ring when taken together, $R^3$ represents an ester-forming functional group selected from the group consisting of —COOR$^5$ and —OR$^5$, in which $R^5$ represents a hydrogen atom or a hydrocarbon group having 1 to 12 carbon atoms which may contain at least one hydroxyl group, $A^1$ and $A^2$ may the same or different and represent bivalent hydrocarbon groups having 1 to 12 carbon atoms which may contain at least one halogen atom, and $A^3$ represents a quadrivalent hydrocarbon group having 5 or 6 carbon atoms, In a preferred embodiment of this invention the phosphorus compound having the general formula (I) is selected, because it is most readily synthesized. The phosphorus compound having the formula (I) may be synthesized in many ways. For example, the reaction may be written as follows:

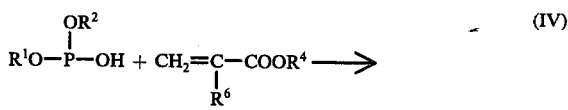

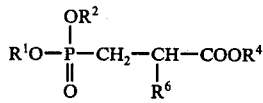

wherein $R^1$, $R^2$ and $R^4$ are the same as defined above, and $R^6$ represents a member selected from the group consisting of hydrogen, halogen, and hydrocarbon groups having 1 to 6 carbon atoms which may contain at least one halogen atom.

This reaction indicates that a phosphite is readily reacted with acrylic acid, an acrylate or a homologue thereof in the presence of a suitable catalyst of a metallic compound such as sodium methoxide and potassium ethoxide to give the compound corresponding to the formula (I) (See, Doklady Akad. Nauk S.S.S.R., vol. 85, 1952, pages 349-352). In practice, either one of, especially both, the phosphite and the acrylic acid, acrylate or homologue thereof used for the synthesis of the destined phosphorus compound may preferably be liquid.

The phosphorus compound which can be used for preparing the flame resistant polyester according to the invention is represented by the above-described formula (I), (II) or (III) and contains at least two ester-forming functional groups. The term "ester-forming functional group" as used herein means groups capable of making a bond with a molecular chain of polyester, for example, —$OR^1$, —$OR^2$ and —$R^3$ in the above formulae.

Examples of $R^1$, $R^2$, $R^3$, $R^4$, $A^1$, $A^2$ and $A^3$ in the above formulae will be listed hereinafter.

Examples of $R^1$, $R^2$ and $R^4$ include hydrogen; lower alkyl groups such as methyl, ethyl, n-propyl, isopropyl, n-butyl, isobutyl, tertiary butyl, etc; haloalkyl groups such as chloromethyl, 2-chloroethyl, 2,3-dichloropropyl, bromomethyl, 2-bromoethyl, 2,3-dibromopropyl, etc.; aryl groups such as phenyl, naphthyl, 2-chlorophenyl, 2-cresyl, etc; benzyl; cyclohexyl and the like. When $R^1$ and $R^2$ are taken together to form a ring, included are alkylene groups such as ethylene, 1,3-propylene, etc.

Examples of $R^3$ include a carboxyl group; alkoxycarbonyl groups such as methoxycarbonyl, ethoxycarbonyl, isopropoxycarbonyl, etc; hydroxyalkoxycarbonyl groups such as hydroxyethoxycarbonyl, hydroxypropoxycarbonyl, etc. Besides, there are also included a hydroxyl group and hydroxyalkoxy groups such as hydroxymethoxy, hydroxyethoxy, 2-hydroxypropoxy, etc.

Examples of $A^1$ and $A^2$ include lower alkylene groups such as methylene, ethylene, 1,2-propylene, 1,3-propylene, 1,4-butylene, etc.; haloalkylene groups such as chloroethylene, bromoethylene, etc.; cycloalkylene groups such as 1,1-cyclohexylene, 1,4-cyclohexylene, etc.; arylene groups such as 1,3-phenylene, 1,4-phenylene, etc.; and the like.

Examples of $A^3$ include quadrivalent hydrocarbon groups represented by the following structural formulae:

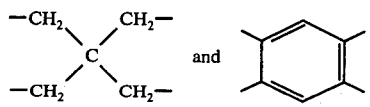

Therefore, specific examples of the phosphorus compounds having the above-described general formulae (I), (II) and (III), respectively, employed herein include methoxycarbonylmethyl dimethyl phosphonate, ethoxycarbonylmethyl dimethyl phosphonate, carboxyethyl dimethyl phosphonate, carboxyethyl diethyl phosphonate, methoxycarbonylethyl dimethyl phosphonate, ethoxycarbonylethyl dimethyl phosphonate, ethoxycarbonylethyl diethyl phosphonate, ethoxycarbonylethyl di(2-bromoethyl) phosphonate, hydroxyethoxycarbonylethyl diethyl phosphonate, ethoxycarbonylethyl diphenyl phosphonate, ethoxycarbonylpropyl diethyl phosphonate, ethoxycarbonylbutyl diethyl phosphonate, hydroxymethyl diethyl phosphonate, hydroxyethyl diethyl phosphonate, 4-methoxycarbonylphenyl dimethyl phosphonate, methoxycarbonylethyl methylethyl phosphonate, ethoxycarbonylethyl methylethyl phosphonate, the compounds represented by the following structural formulae, respectively, and the like.

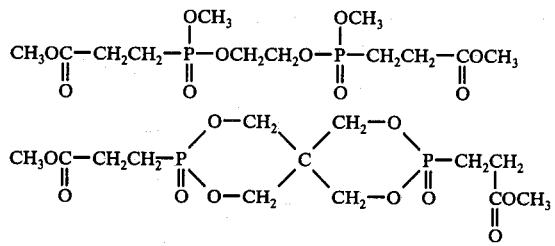

During the preparation of the polyester, the addition of such a phosphorus compound in the reaction system will increase the concentration of hydrogen ions in the system, which tends to inactivate the catalyst used and deteriorate the tone and melt spinnable properties of the resultant polyester. This undesirable tendency is further enhanced, if a phosphorus compound having an acid value above a certain limit is used. The acid value of a phosphorus compound is determined with use of a solution of the same in ethylene glycol. It has been found that the said limit on the acid value is 0.7 equivalent weight/mole. Therefore, it is desirable to use a phosphorus compound having an acid value below the said limit, practically below 0.5 equivalent weight/mole. Alternatively, it is desirable to refine a phosphorus compound having a higher acid value so as to lower its acid value below the said limit, if possible.

In the process for preparing the flame resistant polyester in accordance with this invention, the phosphorus compound as defined above is added to the reaction system so as to give a content of phosphorus in the range of about 500 to about 50,000 ppm in the resultant polyester. Since the loss of the phosphorus compound by dissipation, which is considerably larger in the prior art, is very small in accordance with this invention, the content of phosphorus in the resultant polyester substantially depends on the amount of the phosphorus compound added to the reaction system. Therefore, the amount of the phosphorus compound added can be determined in terms of the use of the resultant polyester, provided that the content within the above-defined range is maintained. If the content of phosphorus in the resultant polyester exceeds 50,000 ppm, an economical disadvantage appears owing to an increase in the amount of the phosphorus compound used and physical properties of the resultant polyester, especially properties required for using it as fiber fail. On the other hand, if the content of phosphorus is less than 500 ppm, no satisfactory flame resistance of the resultant polyester can be achieved.

Examples of the aromatic dicarboxylic acid and the ester-forming derivative thereof employed for the preparation of the flame resistant polyester of this invention include a dicarboxylic acid selected from the group consisting of terephthalic acid, isophthalic acid, 1,4-naphthalene dicarboxylic acid, 2,6-naphthalene dicarboxylic acid and 1,2-bis(4-carboxyphenoxy)ethane, and lower-alkyl esters thereof. If it is desired to obtain a polyester spinnable into a flame resistant fiber, terephthalic acid and lower-alkyl esters thereof are most preferable.

Together with the above-listed aromatic dicarboxylic acid or ester thereof other acids or esters thereof may be used in small amounts, provided that the latter is less than 10 mole % of the former. Such compatible acids and esters thereof are, for example, aromatic dicarboxylic acids such as 2,5-dibromoterephthalic acid, tetrabromoterephthalic acid, 2,2-bis(4-carboxyphenyl)propane, bis(4-carboxyphenyl)-sulfone, bis(4-carboxyphenyl)ether, 2,2-bis(3,5-dibromo-4-carboxyphenyl)-propane, bis(3,5-dibromo-4-carboxyphenyl)sulfone, 4,4'-dicarboxybiphenyl, 3,5-dicarboxybenzene sodium sulfonate, etc. and lower-alkyl esters thereof; and aliphatic dicarboxylic acids such as adipic acid, suberic acid, azelaic acid, sebacic acid, etc.

In addition, oxycarboxylic acids such as 4-hydroxybenzoic acid, 4-hydroxyethoxybenzoic acid and ester-forming derivatives thereof may also be used in small amounts (less than 10 mole %) together with the above-listed aromatic dicarboxylic acid or ester thereof.

Examples of the diol and the ester-forming derivative thereof employed for the preparation of the flame resistant polyester of this invention include aliphatic glycols such as ethylene glycol, 1,2-propylene glycol, trimethylene glycol, tetramethylene glycol, neopentyl glycol, etc., alicyclic glycols such as 1,4-cyclohexane dimethanol, 1,4-cyclohexane diol, etc., and glycols having one or more aromatic rings and represented by the formulae:

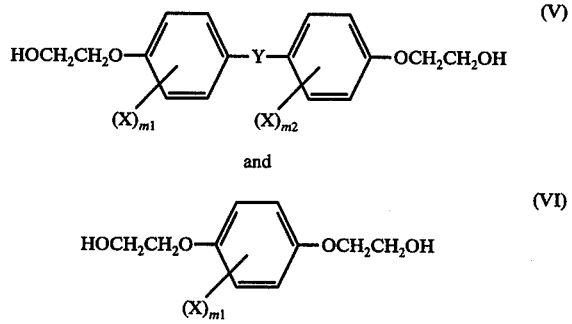

respectively, wherein X represents a halogen atom, Y represents a bivalent group selected from the group consisting of alkylene groups, alkylidene groups, cycloalkylidene groups, arylalkylidene groups each having 1 to 6 carbon atoms, —O—, —S—, —SO— and —SO$_2$—, and m$_1$ and m$_2$ are independently integers of 1 to 4.

Among the above-listed diols are most preferred alkylene glycols having not more than 5 carbon atoms and 1,4-cyclohexane dimethanol.

It is preferable to use a glycol represented by the general formula (V) as a part of the diol contents for preparing a polyester, because halogen atoms are contained in the resultant polyester, which thus exhibits the increased flame resistance. Specific examples of the glycol represented by the general formula (V) include 2,2-bis(3,5-dibromo-4-hydroxyethoxyphenyl)propane, bis(3,5-dibromo-4-hydroxyethoxyphenyl)sulfone, 2,2-bis(3,5-dichloro-4-hydroxyethoxyphenyl)propane, etc.

Together with the above-listed diol or ester thereof other glycols may be used, provided that the latter is less than 10 mole % of the former. Such compatible glycols are, for example, diethylene glycol, polyoxyethylene glycol, ethylene thioglycol, 2-dimethylaminomethyl-2-methyl-1,3-propanediol, etc.

The flame resistant polyester of this invention can be prepared from the above-described aromatic dicarboxylic acid or the ester-forming derivative thereof, the diol or the ester-forming derivative thereof, and the phosphorus compound having at least two ester-forming functional groups in any non-limiting manner. For the preparation of the flame resistant polyester, either the "ester exchange reaction" or the "direct esterification" can be adopted. In the former process, for example, the ester exchange reaction of dimethyl terephthalate with ethylene glycol is carried out to give bis(2-hydroxyethyl)terephthalate, which is then subjected to condensation polymerization to yield polyethylene terephthalate; and in the latter process, for example, terephthalic acid is esterified with ethylene glycol to give bis(2-hydroxyethyl) terephthalate, which is then subjected to condensation polymerization to yield polyethylene terephthalate.

In accordance with this invention the phosphorus compound having the formula (I), (II) or (III) is copolymerized with polyester. It should be carefully selected when the phosphorus compound is to be added, because the efficient introduction of the same in the resultant polyester is of advantage. If it is the only purpose to efficiently introduce the phosphorus compound in the polyester, the phosphorus compound can be added to the reaction system during the ester exchange reaction or esterification, preferably at an initial stage of this reaction. It is to be noted that the phosphorus compound added, in general, tends to deactivate the catalyst used for the ester exchange reaction or esterification, retarding the reaction. Therefore, if a combination of a catalyst and a phosphorus compound requires, it is possibly preferred to add the phosphorus compound to the reaction system at an intermediate stage of the ester exchange reaction or esterification, that is, in the progress of condensation polymerization.

It has been found that the satisfactory flame resistant polyester of this invention can be prepared without any problems by carrying out the ester exchange reaction or esterification and subsequently the condensation polymerization in a conventional manner, while the phosphorus compound can be added to the reaction system at an initial stage of the ester exchange reaction or esterification. This is based on the recognition of the fact that the influence of the phosphorus compound added can be obviated by using a specific catalyst selected for the ester exchange reaction or esterification. This specific catalyst is a compound of a metal belonging to the subgroup of the fourth period in the periodic table, including compounds of a metal selected from the group consisting of titanium, manganese, cobalt and zinc. Among these are most preferred titanium compounds, for example, titanium oxalate; salts of titanyl oxalate such as lithium, potassium, sodium, calcium, magnesium, zinc and ammonium titanyl oxalates, etc; salts of titanium tartrate such as potassium titanium tartrate and ammonium titanium tartrate, etc; titanium alcoholates such as titanium tetraisopropoxide, tetrabutoxide and ethylene glycol ether, etc; acetylacetonatotitanium and the like. Examples of manganese, cobalt, and zinc compounds are salts of inorganic acids such as carbonates, hydrochlorides, sulfates, borates, etc. and salts of organic acids such as formates, acetates, propionates, citrates, oxalates, etc.

A combination of a titanium compound with manganese, cobalt, and zinc compounds is preferable.

Amounts of each catalyst used should be selected so that they satisfy the following formulae (VII) and (VIII), if the content of phosphorus which depends on the amount of the added phosphorus compound having the formula (I), (II) or (III) is less than 7,000 ppm in the resultant polyester.

$$0.2 p^2 + 0.015 \leq x \leq p \quad \text{(VII)}$$

$$y \leq 0.3p - 0.25x \quad \text{(VIII)}$$

(wherein $p$, $x$, and $y$ are determined on the basis of the weight of the resultant polyester, $p$ represents in wt % the content of phosphorus resulting from the added phosphorus compound, $x$ represents in wt % the total amount of manganese, cobalt and zinc resulting from the used compounds thereof, and $y$ represents in wt % the amount of titanium resulting from the used compound thereof.)

It is very important for the manufacture of fiber from the flame resistant polyester to select the amounts of each catalyst used in accordance with the above-described formulae (VII) and (VIII). Especially, when it is desired to obtain a molded article which is high in whiteness degree and exhibits no discoloration on heating or bleaching, these conditions should be satisfied.

The flame resistant polyester of this invention can easily be prepared in a conventional manner without departing from the normal conditions set for the usual ester exchange reaction or esterification, except that the specific phosphorus compound is to be added and the specific catalysts of metal compounds are preferably used for the ester exchange reaction or esterification. When dimethyl terephthalate and ethylene glycol, for example, are used as starting materials for manufacturing an aromatic polyester, the above-described phosphorus compound and catalysts selected for this reaction are added to the reaction system. The ester exchange reaction is carried out at a temperature of 150° to 230° C in a conventional manner and then the reaction product is subjected to condensation polymerization at an elevated temperature of 260° to 300° C under a reduced pressure of less than 1 mmHg in the presence of a catalyst for condensation polymerization, yielding the flame resistant polyester of destination. Alternatively, when terephthalic acid and ethylene glycol are used as starting materials, the above-described phosphorus compound and catalysts selected for this reaction are added to the reaction system. The esterification is carried out at a temperature of 200° to 300° C, preferably 240° to 270° C under the normal pressure or an applied pressure of less than 5 kg/cm² in a conventional manner, while the water resulting from the esterification is removed out of the reaction system. The resultant reaction product is subjected to condensation polymerization under the same conditions as those described above, yielding the flame resistant polyester of destination. For the condensation polymerization a conventional catalyst selected from antimony and germanium compounds such as antimony trioxide, germanium dioxide, etc. can be used.

When other aromatic polyester-forming reagents are used as starting materials, they can be reacted in a similar manner as described above by appropriately changing conditions so as to accommodate the reagents used, yielding the flame resistant polyester of destination.

It is quite unexpected that the flame resistant polyester of this invention, which contains a comparatively large amount of the phosphorus compound represented by the general formula (I), (II) or (III) and having a number of ester-forming functional groups, can be molded (melt spinnable) into fiber; because a large amount of a phosphorus compound contained in a polyester is considered to cause the gelation of the resultant polyester. This unexpected moldability is ascribed to the fact that reactivities of ester-forming functional groups of the phosphorus compound represented by the formula (I), (II) or (III) are different from each other and the molecular weight of the phosphorus compound is comparatively large so that molecules of the phosphorus compound bond to molecules of the polyester at positions hindered from crosslinking, for example, the terminal positions of the polyester molecules.

Since the phosphorus compound used herein can be added to the reaction system of polyester without deactivating the specific catalyst such as zinc compounds used for the ester exchange reaction or esterification, it is easy to prepare the polyester of this invention, which exhibits sufficient properties to use the same as fiber. Further, the loss of the phosphorus compound by dissipation is reasonably small, though the reaction system is maintained at elevated temperatures under substantially a vacuum during the condensation polymerization. Consequently, the flame resistant polyester of this invention can be prepared by following and slightly modifying the prior procedures for preparing polyesters without any problem.

The phosphorus compounds used herein, particularly the compounds represented by the formula (I) can easily be synthesized. This shows that the flame resistant polyester of this invention can be prepared at a low cost.

As described in the foregoing, this invention also provides an improved process for preparing flame resistant polyesters. In the process it is within the spirit of the invention to admit additives usually employed in the manufacture of polyester, for example, inhibitors against the formation of ether bonds such as aliphatic amines, aliphatic carboxylic acid amides, alkaline metal compounds, etc.; stabilizers such as alkyl-substituted phenols, etc; pigments such as titanium oxide, carbon black, etc.; antistatic agents; plasticizers and the like.

Furthermore, since the flame resistant polyester of this invention exhibits not only an excellent flame resistance, but also other improved properties, it can be used as molded articles such as film and board as well as fiber.

The invention will now be described in further details with reference to the following illustrative, but not limiting, examples. Unless otherwise stated, the "part" in the examples stands for part by weight.

The acid value of a phosphorus compound is determined by potentiometric titration. To this end a solution of a sample of the phosphorus compound in ethylene glycol is titrated with the 0.1 N sodium hydroxide solution.

For the definition of reactivity in the ester exchange reaction, the reaction in which the theoretical amount of methanol has been distilled out within 150 minutes after the initiation of reaction is classified as grade A, 150 to 210 minutes — grade B, and over 210 minutes — grade C.

The intrinsic viscosity of a polymer is calculated on the basis of the determination with use of a phenol-tetrachloroethane (mixing ratio by weight = 3 : 2) solution of the polymer at a temperature of 30° C.

The b value (tone) of a polymer is determined by means of the differential colorimeter, ND-101D, manufactured by Nippon Denshoku Co. on a filament obtained by melt spinning the polymer and then drawing.

The flame resistance of a polymer is determined as follows. Yarns consisting of drawn filaments are knitted into knitted goods. A 1-g sample of the knitted goods is made round into a cylindrical sample having a length of 10 cm, which is inserted into a wire coil having a diameter of 10 mm so that the sample cylinder is supported at an angle of 45° C with the vertical. The sample is ignited at the lower end. After the ignition the fire source is immediately removed and the sample on combustion is carefully observed. If the flame ceases to exist halfway, the ignition is carried out again in the same manner and the number of ignitions required to burn down the whole sample is counted. The average number of ignitions of five samples shows the flame resistance.

The discoloration of a polymer is determined as follows. A sample of knitted goods as described above is dyed under the following conditions:

| Dye bath | |
|---|---|
| Miketon Polyester Red 2BSF | 2%owf |
| Bath ratio | 1/100 |
| Disper TL | 1g/l |
| Temperature | 120° C |
| Time | 60 min. |

The dyed sample is hot-pressed at a temperature of 150° C for two minutes. It is determined whether the discoloration has occurred or not.

PREPARATION EXAMPLE 1

Into a 2 l, 4-necked flask equipped with a stirrer, a reflux condenser, a thermometer and a dropping funnel was placed a mixture of 5500 g of dimethyl hydrogenphosphite and 4300 g of methyl acrylate. With rapid stirring, 80 g of methanol containing 2 N sodium methoxide was introduced through the dropping funnel over 60 minutes. As the reaction proceeded it was necessary to absorb part of the reaction heat by surrounding the reaction vessel with a water bath, maintaining the temperature in the vessel below 80° C. After the solution methoxide had been added, the contents were allowed to stand for 10 minutes. Thereafter, unreacted dimethyl hydrogenphosphite, methyl acrylate and others were distilled out under reduced pressures and there remained the reaction product. This crude product was further purified by distillation, yielding 8100 g of methoxycarbonylethyl dimethyl phosphonate, chemical properties of which were found as follows.

boiling point: 143° – 145° C/10 mmHg
$n_D^{30}$: 1.4327
acid value: below 0.01 equiv. wt/mole

PREPARATION EXAMPLE 2

Preparation Example 1 was repeated except that a mixture of 5520 g of diethyl hydrogenphosphite and 4000 g of ethyl acrylate was used. The resultant reaction product was purified by distillation, yielding 8000 g of ethoxycarbonylethyl diethyl phosphonate, chemical properties of which were found as follows.

boiling point: 152° – 154° C/10 mmHg
$n_D^{30}$: 1.4287
acid value: 0.01 equiv. wt/mole

EXAMPLE 1

Into a reaction vessel equipped with a stirrer, a condenser, a thermometer and an evacuating tube connected to a vacuum pump was placed a mixture of 194 parts of dimethyl terephthalate, 124 parts of ethylene glycol, 6.6 parts of ethoxycarbonylethyl diethyl phosphonate (obtained in Preparation Example 2), 0.12 part of potassium titanyl oxalate and 0.03 part of antimony trioxide. The reaction vessel was heated to a temperature of 150° C to initiate the ester exchange reaction. Further heat was applied to gradually increase the temperature, reaching 230° C after 150 minutes. This application of heat enabled the theoretical amount of methanol to be distilled out within said period of time. Then the reaction vessel was gradually heated up to 275° C over a period of 40 minutes, while the same was slowly evacuated to 0.2 mmHg. Under these conditions the condensation polymerization was carried out for 100 minutes, yielding the polymer. It was found that the polymer had an intrinsic viscosity of 0.60 and the phosphorus in the added phosphorus compound remained wholly (100%) in the polymer.

This polymer was melt-spun in a conventional manner at a temperature of 290° C and then drawn in a conventional manner into flame resistant filaments. The flame resistance of drawn filament expressed as the number of ignitions was 5.5 times.

COMPARATIVE EXAMPLE 1

Example 1 was repeated except that 3.6 parts of trimethyl phosphate was used in place of ethoxycarbonylethyl diethyl phosphonate. The catalyst for the ester exchange reaction, potassium titanyl oxalate, was immediately deactivated, and thereby the ester exchange reaction did not proceed at all. Consequently, no polyester was obtained.

EXAMPLE 2

Example 1 was repeated except that 2.6 parts of methoxycarbonylethyl dimethyl phosphonate (obtained in Preparation Example 1) was used in place of ethoxycarbonylethyl diethyl phosphonate. There was obtained the polymer, which was then melt-spun and drawn into filaments in a similar manner as described in Example 1.

| Properties of the polymer: | |
|---|---|
| Intrinsic viscosity | 0.58 |
| Ratio of the phosphorus remaining in the polymer to the added | 99 % |
| Properties of the drawn filament: | |
| Tenacity at break | 3.7 g/D |
| Elongation at break | 27 % |
| Flame resistance | 4.5 times |

EXAMPLES 3 – 8

Example 1 was repeated except that the phosphorus compound and catalysts shown in Table 1 were used in different amounts. Properties of the resultant polymers are also shown in Table 1.

Table 1

| | Phosphorus compound | | Amount of Catalyst (part) | | | Properties of Polyester | | | |
|---|---|---|---|---|---|---|---|---|---|
| Example | Name | Amount (part) | Zinc acetate | Potassium titanyl oxalate | Antimony trioxide | Intrinsic viscosity | Ratio of remaining phosphorus (%) | Content of diethylene glycol (mole %) | Flame resistance (Times) |
| 3 | ethoxycarbonylethyl diethyl phosphonate | 3.3 | 0.17 | 0.02 | 0.03 | 0.57 | 100 | 2.7 | 4.4 |
| 4 | phenoxycarbonylethyl diethyl phosphonate | 3.6 | 0.17 | 0.04 | 0.02 | 0.54 | 93 | 2.8 | 4.5 |
| 5 | hydroxyethoxycarbonylethyl diethyl phosphonate | 3.2 | 0.17 | 0.04 | 0.02 | 0.56 | 95 | 2.5 | 4.5 |
| 6 | hydroxyethyl diisopropyl phosphonate | 2.6 | 0.17 | 0.04 | 0.02 | 0.58 | 85 | 3.0 | 4.2 |
| 7 | (a) | 5.6 | 0.17 | 0.03 | 0.02 | 0.57 | 98 | 2.4 | 4.3 |
| 8 | (b) | 7.5 | 0.11 | 0.04 | 0.02 | 0.59 | 100 | 2.5 | 5.0 |

(a) $HOCH_2CH_2OOCH_2CH_2\underset{\underset{O}{\|}}{P}(OCH_3)-OCH_2CH_2O-\underset{\underset{O}{\|}}{P}(OCH_3)-CH_2CH_2COOCH_2CH_2OH$ (b) $CH_3OCCH_2CH_2P\underset{O}{\overset{O}{\|}}\underset{OCH_2}{\overset{OCH_2}{\diagup}}C\underset{CH_2O}{\overset{CH_2O}{\diagdown}}PCH_2CH_2COCH_3$

COMPARATIVE EXAMPLE 2

A mixture of 194 parts of dimethyl terephthalate, 124 parts of ethylene glycol, 0.06 part of zinc acetate and 0.06 part of antimony trioxide was subjected to ester exchange reaction in a similar manner as described in Example 1 and then 6.6 parts of ethoxycarbonylethyl diethyl phosphonate was added thereto. After the contents had been agitated in the nitrogen atmosphere at a temperature of 230° C for 20 minutes, the reaction vessel was heated up to 275° C, while the same was slowly evacuated to 0.2 mmHg. Under these conditions the condensation polymerization was carried out for 95 minutes. While the resultant polymer showed an intrinsic viscosity of 0.65, the ratio of the phosphorus remaining in the polymer to the added amount was as low as 30% and the flame resistance of the drawn filament made of this polymer was 3.5 times.

EXAMPLE 9

Into the reaction vessel used in Example 1 were placed 194 parts of dimethyl terephthalate, 124 parts of ethylene glycol, 5.8 parts of methoxycarbonylethyl dimethyl phosphonate, 1.31 parts of monomethoxypolyethylene glycol (m.w. 900), 0.07 part of ammonium titanyl oxalate, 0.05 part of zinc acetate and 0.03 part of antimony trioxide. The reaction was carried out in accordance with the procedure described in Example 1 to give the polymer. The resultant polymer showed an intrinsic viscosity of 0.59 and a ratio of the remaining phosphorus to the added amount of 97%, and the flame resistance of the drawn filament made of this polymer was 5 times.

EXAMPLE 10

Into the reaction vessel used in Example 1 were placed 194 parts of dimethyl terephthalate, 124 parts of ethylene glycol, 3.3 parts of ethoxycarbonylethyl diethyl phosphonate, 19.4 parts of 2,2-bis(3,5-dibromo-4-hydroxy ethoxyphenyl) propane, 0.07 part of potassium titanyl oxalate, 0.03 part of zinc acetate and 0.04 part of antimony trioxide. The reaction was carried out in accordance with the procedure described in Example 1. In this case the condensation polymerization was continued for 120 minutes. The resultant polymer showed an intrinsic viscosity of 0.53 and a ratio of the remaining phosphorus to the added amount of 100%, and the flame resistance of the drawn filament made of this polymer was more than 6 times.

COMPARATIVE EXAMPLE 3

Example 10 was repeated except that 2.6 parts of benzene diethyl phosphonate were used in place of ethoxycarbonylethyl diethyl phosphonate. The resultant polymer showed an intrinsic viscosity of 0.57, the ratio of the remaining phosphorus to the added amount was very low such as only 15%, and the flame resistance of the drawn filament made of this polymer was 4 times.

EXAMPLE 11

Into a reaction vessel equipped with a stirrer, a distillation column, a thermometer and a pressure regulator was placed a mixture of 166 parts of terephthalic acid, 130 parts of ethylene glycol, 4.8 parts of ethoxycarbonylethyl diethyl phosphonate, 0.12 part of potassium titanyl oxalate, 0.05 part of sodium acetate and 0.03 part of antimony trioxide. The esterification was carried out at a temperature of 230° C under a gauge pressure of 2.5 kg/cm² for two hours, while the water formed during the esterification as a by-product is continuously distilled out of the vessel. The resultant reaction product was then placed in a vessel for condensation polymerization, which was heated up to 275° C and slowly evacuated to 0.2 mmHg. Under these conditions the condensation polymerization was carried out for 100 minutes, yielding the polymer. It was found that the polymer had an intrinsic viscosity of 0.55 and the phosphorus in the added phosphorus compound remained wholly (100%) in the polymer. The flame resistance of the drawn filament made of this polymer was 4.5 times.

EXAMPLE 12

Into the reaction vessel used in Example 1 was placed a mixture of 144.5 parts of dimethyl terephthalate, 185.0 parts of 1,4-cyclohexane dimethanol, 6.5 parts of methoxycarbonylethyl diisopropyl phosphonate and 0.28 part of ammonium titanyl oxalate. The vessel was heated to a temperature of 160° C to initiate the ester exchange reaction. Additional heat was applied to gradually increase the temperature, reaching 275° C after 110 minutes, while the theoretical amount of methanol had been distilled out within said period of time. Then the reaction vessel was gradually heated up to 315° C over a period of 40 minutes, while the same was slowly evacuated to 0.2 mmHg. Under these conditions the condensation polymerization was carried out for 120 minutes, yielding the white polymer. It was found that the polymer had an intrinsic viscosity of 0.56 and a melting point of 288° – 293° C and the phosphorus in the added phosphorus compound remained wholly (100%) in the polymer. The flame resistance of the drawn filament made of this polymer was 4.5 times.

EXAMPLE 13

Into the reaction vessel used in Example 1 was placed a mixture of 116.4 parts of dimethyl terephthalate, 29.1 parts of dimethyl isophthalate, 200 parts of 1,4-cyclohexane dimethanol, 4.8 parts of methoxycarbonylethyl dimethyl phosphonate and 0.18 part of titanium tetrabutoxide. The vessel was heated to a temperature of 160° C to initiate the ester exchange reaction. Additional heat was applied to gradually increase the temperature, reaching 250° C after 90 minutes, while the theoretical amount of methanol had been distilled out within said period of time. Then the reaction vessel was gradually heated up to 295° C over a period of 40 minutes, while the same was slowly evacuated to 0.2 mmHg. Under these conditions the condensation polymerization was carried out for 100 minutes, yielding the white polymer. It was found that the polymer had an intrinsic viscosity of 0.58 and a melting point of 260° – 265° C and the ratio of the phosphorus remaining in the polymer to the added amount was 96%. The flame resistance of the drawn filament made of this polymer was 4.2 times.

EXAMPLES 14 – 17

Into the reaction vessel used in Example 1 was placed a mixture of 174.6 parts of dimethyl terephthalate, 111.6 parts of ethylene glycol, 2.8 parts of ethoxycarbonylethyl diethyl phosphonate and the predetermined amounts of catalysts shown in Table 2. The vessel was heated to a temperature of 150° C to initiate the ester exchange reaction. Additional heat was applied to gradually increase the temperature to 230° C until the theoretical amount of methanol had been distilled out. Then the reaction vessel was heated up to 275° C over a period of 40 minutes, while the same was evacuated to 0.1 mmHg. Under these conditions the condensation polymerization was carried out for 30 minutes, yielding the polymer. The results are shown in Table 2.

Table 2

| Example | Amount of catalyst (part) | | | Period ester exchange reaction (min) | Polymer | | Drawn filament | | |
|---|---|---|---|---|---|---|---|---|---|
| | Zinc acetate | Potassium titanyl oxylate | Antimony trioxide | | Intrinsic viscosity | Ratio of remaining phosphorus (%) | Tone (b value) | Flame resistance (times) | Discoloration |
| 14 | 0.10 | 0.05 | 0.02 | 115 | 0.56 | 100 | 3 | 4.5 | not discolored |
| 15 | 0.17 | | 0.04 | 110 | 0.55 | 95 | 2 | 4.3 | " |
| 16 | | 0.10 | 0.02 | 185 | 0.57 | 95 | 6 | 4.3 | " |
| 17 | 0.44 | | 0.04 | 95 | 0.52 | 95 | 3 | 4.3 | discolored |

EXAMPLE 18

Into the reaction vessel used in Example 1 was placed a mixture of 174.6 parts of dimethyl terephthalate, 111.6 parts of ethylene glycol, 2.8 parts of ethoxycarbonylethyl diethyl phosphonate, 0.35 part of calcium acetate and 0.04 part of antimony trioxide. The vessel was heated to a temperature of 150° C to initiate the ester exchange reaction. Since the rate of distillation of methanol had decreased to an insufficient level at an intermediate stage, another portion (0.35 part) of calcium acetate was added to catalyze the reaction again. It took 240 minutes for the ester exchange reaction to be completed. The reaction product was subjected to condensation polymerization in accordance with the procedure described in Examples 14 – 17, yielding the polymer. It was found that the polymer had an intrinsic viscosity of 0.48 and the ratio of the phosphorus remaining in the polymer to the added amount was 95%. The flame resistance of the drawn filament made of this polymer was 3.5 times.

EXAMPLE 19 – 22

The crude ethoxycarbonylethyl diethyl phosphonate obtained in Example 2 was mixed with the purified in various proportions to prepare samples having different acid values.

Into the reaction vessel used in Example 1 was placed a mixture of 194 parts of dimethyl terephthalate, 124 parts of ethylene glycol, 3.1 parts of an ethoxycarbonylethyl diethyl phosphonate sample having the acid value shown in Table 3 and the predetermined amounts of catalysts also shown in Table 3. The vessel was heated to a temperature of 150° C to initiate the ester exchange reaction. Additional heat was applied to gradually increase the temperature to 230° C until the theoretical amount of methanol had been distilled out. Then the reaction vessel was heated up to 275° C over a period of 40 minutes, while the same was evacuated to 0.1 mmHg. Under these conditions the condensation polymerization was carried out for 30 minutes, yielding the polymer. The results are shown in Table 3.

EXAMPLE 23 – 24

Into the reaction vessel used in Example 1 was placed a mixture of 194 parts of dimethyl terephthalate, 124 parts of ethylene glycol and 0.06 part of zinc acetate and 0.04 part of antimony trioxide as catalysts. The vessel was heated to a temperature of 150° C to initiate the ester exchange reaction. Additional heat was applied to increase the temperature to 230° C until the theoretical amount of methanol had been distilled out. At this stage 3.1 parts of ethoxycarbonylethyl diethyl phosphonate having the acid value shown in Table 3 was added and then the condensation polymerization was carried out in accordance with the procedure described in Examples 16-19, yielding the polymer. The results are shown in Table 3.

Table 3

| Example | Acid value of ethoxycarbonyl-ethyl diethyl phosphonate (equiv. wt/mole) | Amount of catalyst (part) | | | Reactivity in ester exchange reaction (grade) | Properties of polyester | | | |
|---|---|---|---|---|---|---|---|---|---|
| | | Zinc acetate | Potassium titanyl oxalate | Antimony trioxide | | Intrinsic viscosity | Ratio of remaining phoshorus (%) | Content of diethylene glycol (%) | Flame resistance (times) |
| 19 | <0.01 | 0.11 | — | 0.04 | A | 0.58 | 259 | 2.0 | 4.5 |
| 20 | 0.10 | 0.11 | 0.10 | 0.04 | A | 0.58 | 258 | 2.7 | 4.5 |
| 21 | 0.30 | 0.11 | 0.20 | 0.04 | B | 0.56 | 255 | 3.5 | 4.4 |
| 22 | 0.50 | 0.11 | 0.20 | 0.04 | B | 0.54 | 254 | 4.0 | 4.0 |
| 23 | 0.70 | 0.06 | — | 0.08 | C | 0.52 | 252 | 5.2 | 3.8 |
| 24 | 0.80 | 0.06 | — | 0.08 | C | 0.52 | 248 | >6.0 | 3.0 |

What is claimed is:

1. A flame resistant polyester comprising a polymer prepared by polymerizing an aromatic dicarboxylic acid or an ester-forming derivative thereof, a diol or an ester-forming derivative thereof, and at least one phosphorus compound selected from the group consisting of compounds having the formulae (I), (II), and (III):

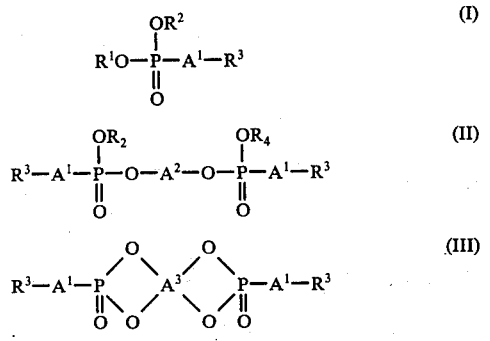

wherein $R^1$, $R^2$, and $R^4$ may be the same or different and represent hydrogen atoms or hydrocarbon groups having 1 to 18 carbon atoms which may contain at least one halogen atom, $R^1$ and $R^2$ being capable of forming a ring when taken together, $R^3$ represents the ester-forming functional group —COOR$^5$, in which $R^5$ represents a hydrogen atom or a hydrocarbon group having 1 to 12 carbon atoms which may contain at least one hydroxyl group, $A^1$ and $A^2$ may be the same or different and represent bivalent hydrocarbon groups having 1 to 12 carbon atoms which may contain at least one halogen atom, and $A^3$ represents a quadrivalent hydrocarbon group having 5 or 6 carbon atoms, the content of phosphorus in the polymer being in a range of about 500 to about 50,000 ppm.

2. The flame resistant polyester as claimed in claim 1 wherein the phosphorus compound having the formula (I) is used.

3. The flame resistant polyester as claimed in claim 1 wherein the phosphorus compound having the general formula (I) in which $A^1$ is a lower alkylene group having 1 to 4 carbon atoms is used.

4. The flame resistant polyester as claimed in claim 1 wherein the phosphorus compound having the formula (I) in which $R^3$ is —COOR$^7$ and $R^7$ is selected from the group consisting of hydrogen, methyl, ethyl, isopropyl, tertiary butyl, and 2-hydroxyethyl is used.

5. The flame resistant polyester as claimed in claim 2 wherein the phosphorus compound having the formula (I) is methoxycarbonylethyl dimethyl phosphonate or ethoxycarbonylethyl diethyl phosphonate.

6. The flame resistant polyester as claimed in claim 1 wherein said aromatic dicarboxylic acid or the ester-forming derivative thereof is terephthalic acid or an ester-forming derivative thereof and said diol or the ester-forming derivative thereof is at least one glycol selected from the group consisting of alkylene glycols having not more than 5 carbon atoms and 1,4-cyclohexane dimethanol.

7. The flame resistant polyester as claimed in claim 1 wherein said diol or the ester-forming derivative thereof is, not exclusively, a glycol having the formula:

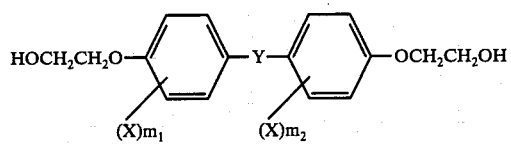

wherein X represents a halogen atom, Y represents a bivalent group selected from alkylene and alkylidene groups having 1 to 6 carbon atoms, —O—, —SO— and —SO$_2$—, and $m_1$ and $m_2$ are integers of 1 to 4, respectively.

8. The flame resistant polyester as claimed in claim 1 wherein at least one compound of a metal selected from the group consisting of zinc, manganese, cobalt and titanium is used as a catalyst for the esterification or ester exchange reaction in the course of the preparation of said polymer.

9. Flame resistant fiber manufactured by the melt spinning of the polyester of claim 1.

* * * * *